US00PP24399P2

(12) United States Plant Patent
Handyside

(10) Patent No.: US PP24,399 P2
(45) Date of Patent: Apr. 22, 2014

(54) ***PHORMIUM* PLANT NAMED 'BLONDIE'**

(50) Latin Name: *Phormium cookianum*
Varietal Denomination: BLONDIE

(76) Inventor: Paul Robert Handyside, Tauranga (NZ)

( * ) Notice: Subject to any disclaimer, the term of this patent is extended or adjusted under 35 U.S.C. 154(b) by 268 days.

(21) Appl. No.: 13/374,895

(22) Filed: Jan. 23, 2012

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

PUBLICATIONS

PLUTO UPOV, Plant Variety Database 201303 retrieved on Nov. 18, 2013 from the internet at <https://www3.wipo.int/pluto/user/en/index.jsp> PBR FLX020, published in New Zealand, in Jan. 14, 2007. 3 pp.*

*Phormium* hybrids 'Blondie', retrieved on Dec. 4, 2013 from the internet at <http://www.boethingtreeland.com/flower-color/yellow/phormium-hybrids-blondie.html>, published by Boething Treeland Farms Inc., 2013. 2 pp.*

* cited by examiner

*Primary Examiner* — June Hwu
*Assistant Examiner* — Louanne Krawczewicz Myers

(57) ABSTRACT

A new cultivar of *Phormium* plant named 'BLONDIE' that is characterized by pronounced arching habit and leaves which are long and narrow and strongly reflexed. The leaves of 'BLONDIE' are variegated, consisting of predominantly cream colored leaf blades within bands of green which are themselves bordered by thin greyed-purple outer margins. 'BLONDIE' has a multiplication rate between six-fold and eight-fold in each season and is hardy to USDA Zone 7. No flowers have been observed on mature plants of 'BLONDIE' to date. In combination these traits set 'BLONDIE' apart from all other existing varieties of *Phormium* known to the inventor.

3 Drawing Sheets

Genus: *PHORMIUM.*
Species: *Cookianum.*
Denomination: 'BLONDIE'.

BACKGROUND OF THE INVENTION

The present invention relates to a new and distinct variety of New Zealand flax grown for use in the landscape, or for use as a container plant. The new cultivar is known botanically as *Phormium cookianum* and will be referred to hereinafter by the cultivar name 'BLONDIE'.

The new *Phormium* cultivar named 'BLONDIE' is a naturally occurring whole plant mutation that was discovered by the inventor in 2005 in Tauranga, New Zealand as single plant within the inventor's commercial crop of *Phormium cookianum* 'Cream Delight' (unpatented). The inventor observed that one plant, later named 'BLONDIE', was shorter than all other plants in the crop and produced exceptionally reflexing leaves, which were also narrower than the leaves of 'Cream Delight'. The inventor continued to observe this one plant and found that these differences from 'Cream Delight' became more pronounced as the growing season progressed. Within one year of growth, the leaves of the discovered plant became so fully reflexed that the tips of the leaves extended considerably below the level of the base of the plant.

'BLONDIE' exhibits a clumping habit comprised of narrow leaves which tend to arch from earliest growth. 'BLONDIE' was first asexually propagated by the inventor in Tauranga, New Zealand in 2005 by division of the initially-discovered plant. *Phormiums* are relatively slow to multiply and by 2011 the inventor had produced approximately six thousand plants of 'BLONDIE' by repeated division of each new generation with no instances of reversion or variation in habit. The inventor has determined that 'BLONDIE' is stable and reproduces true to type in successive generations of asexual propagation.

The closest variety of *Phormium* known to the inventor is the parent variety *Phormium* 'Cream Delight'. 'Cream Delight' and 'BLONDIE' have similarly variegated cream-green foliage. However, the leaves of 'BLONDIE' are strongly reflexed and are narrow, being approximately one third of the width of the leaves of 'Cream Delight'. In addition, the inventor has observed that 'BLONDIE' exhibits a more prolific multiplication rate than 'Cream Delight'. Whereas a single basal fan of 'Cream Delight' will increase two-fold to three fold in one growing season, the multiplication rate of 'BLONDIE' ranges between six-fold and eight-fold, which is an important commercial distinction and benefit.

Cultural requirements for the production of 'BLONDIE' include growing in full sun to part shade, occasional to regular water but avoiding drying out or excess water in the potting mix which should be free-draining. The inventor has not observed any particular susceptibility or resistance to pests and diseases. The inventor has not observed any flowers on any plants of 'BLONDIE' to date, including plants which are five or six years old.

The inventor filed an application for New Zealand Plant Breeders' Rights for 'BLONDIE' on Nov. 20, 2006, Serial Number FLX020. Since that time, all plants of 'BLONDIE' remained under the inventor's and applicant's control until the first liners (one year old divisions) were sold to wholesale growers in New Zealand in April 2011 and to wholesale growers in the USA in May 2011.

SUMMARY OF THE INVENTION

The following traits have been repeatedly observed and represent the distinguishing characteristics of the new *Phormium* variety named 'BLONDIE'. In combination these traits set 'BLONDIE' apart from all other *Phormium* known to the inventor. 'BLONDIE' has not been tested under all possible conditions and phenotypic differences may be observed with variations in environmental, climatic and cultural conditions, however, without any variance in genotype.

1. 'BLONDIE' exhibits a pronounced arching habit.
2. The foliage of 'BLONDIE' is long and narrow and strongly reflexed.
3. The foliage of 'BLONDIE' is variegated, consisting of predominantly cream colored leaf blades within bands of green which are themselves bordered by thin greyed-purple outer margins.
4. 'BLONDIE' forms a dense clump comprised of numerous fans arising from the base.
5. 'BLONDIE' exhibits stiff leaves that are folded lengthwise. The folds are fused at the base.
6. 'BLONDIE' has a multiplication rate between six-fold and eight-fold in each season.
7. 'BLONDIE' is hardy to USDA Zone 7.
8. 'BLONDIE' has produced no flowers to date.

BRIEF DESCRIPTION OF THE DRAWINGS

The accompanying color drawings illustrate the overall appearance of the new *Phormium* cultivar named 'BLONDIE' showing the colors as true as it is reasonably possible to obtain in colored reproductions of this type. Colors in the drawings may differ from the color values cited in the detailed botanical description, which accurately describes the actual colors of the new variety 'BLONDIE'. All drawings were made at the inventor's nursery in Tauranga, New Zealand.

Figure 1:
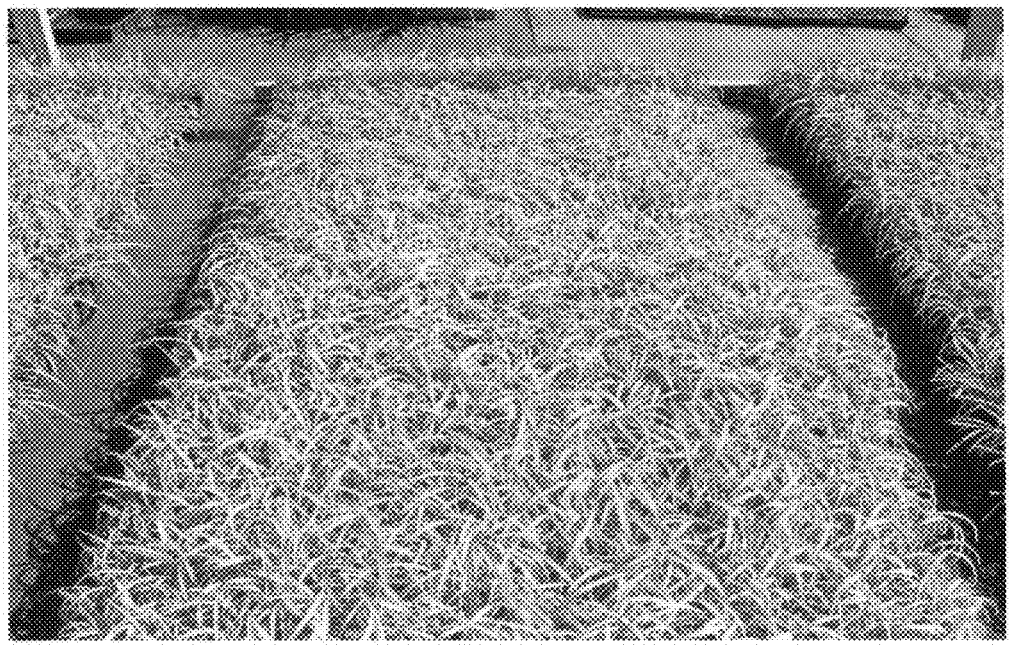
FIG. 1 illustrates the inventor's stock which has been multiplied by division from the initially discovered variety. All plants are identical, with no reversion or off-types.
Figure 2:
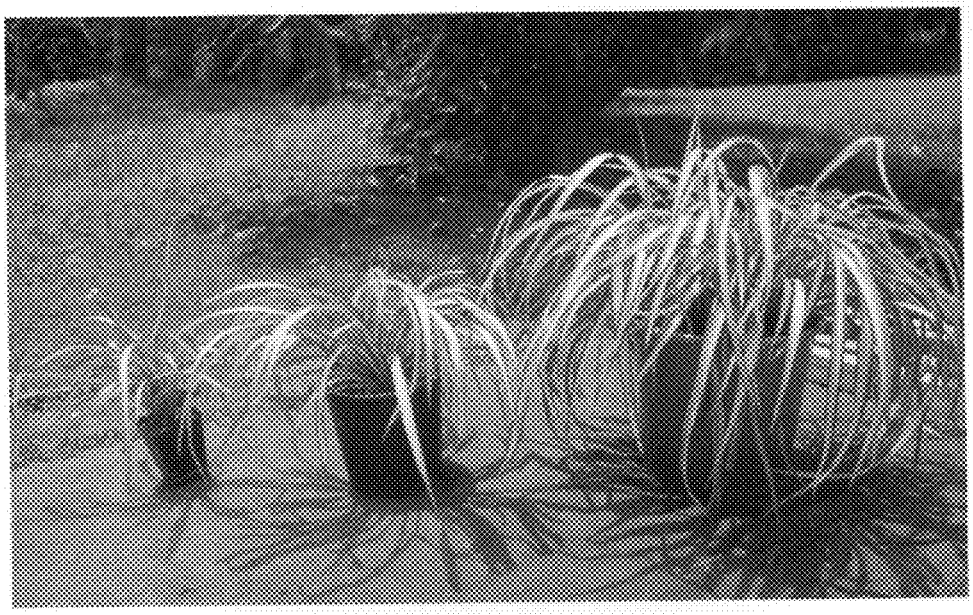
FIG. 2 illustrates plants of 'BLONDIE' at one year, two years and three years from the initial division.
Figure 3:
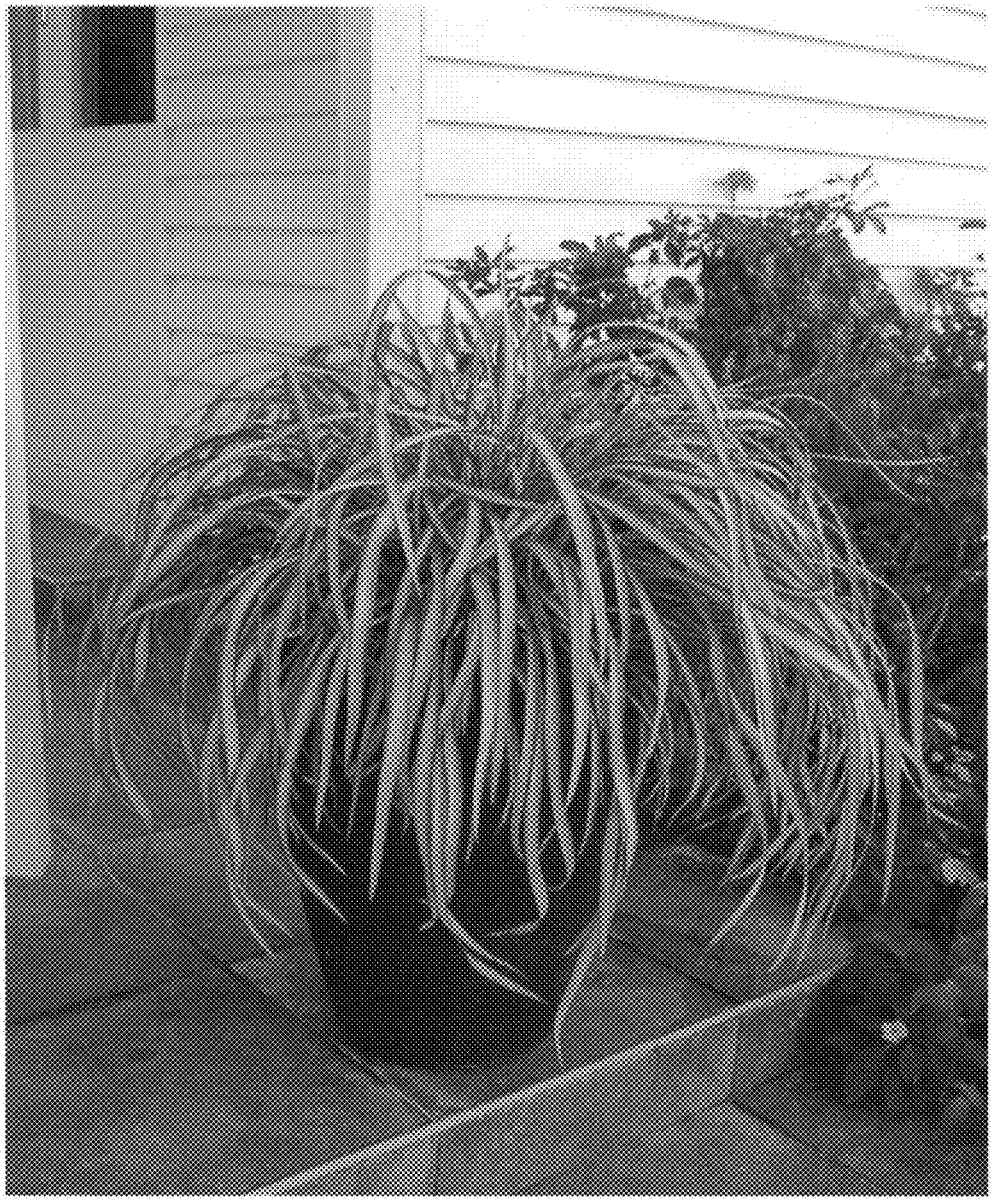
FIG. 3 illustrates a four year old mature plant of 'BLONDIE' which has been transplanted into a 25 cm diameter container.

All plants illustrated in the drawings have been grown out of doors in Tauranga, New Zealand.

DETAILED BOTANICAL DESCRIPTION

The following is a detailed description of the new *Phormium* plant named 'BLONDIE'. Data was collected in Santa Barbara, Calif. from one year old plants growing in full sun out-of-doors in deep 4 inch commercial containers. The color determinations are in accordance with the fifth edition (2007) of The Royal Horticultural Society Colour Chart, of London, England, except where general color terms of ordinary dictionary significance are used.

Botanical classification: *Phormium cookianum* 'BLONDIE'.

Genus: *PHORMIUM.*

Species: *Cookianum.*

Denomination: 'BLONDIE'.

Common name: New Zealand flax.

Plant type: Perennial container plant in USDA Zone 7 and warmer; annual in colder regions.

Recommended container size: A commercial propagator of 'BLONDIE' may produce starter plants for others in sizes ranging from 5 cm to 10 cm. A grower of finished plants for sale to the public may produce 'BLONDIE' in any size container from a US 1 gallon upwards.

Plant use: Recommended for use in the landscape, or for use as a container plant.

Cultural requirements: Cultural requirements are full sun to partial shade, occasional to regular water, and well-draining loam soil.

Parentage: *Phormium cookianum* 'BLONDIE' was discovered as a naturally occurring individual whole plant mutation within a commercial crop of *Phormium cookianum* 'Cream Delight'.

Disease and pest susceptibility or resistance: None observed by the inventor.

Plant description:

*Plant habit.*—Arching, clumping.

*Plant vigor.*—Vigorous compared to *Phormium* generally.

*Multiplication rate.*—A single basal fan of 'BLONDIE' increases between six-fold and eight-fold in one growing season.

*Plant height* (*one year*).—20 cm.

*Plant width* (*one year*).—20 cm.

*Plant height* (*five years*).—30 cm.

*Plant width* (*five years*).—60 cm.

*Plant hardiness.*—USDA Zone 7.

*Plant propagation.*—Tissue culture and division.

*Root system.*—Fibrous and fleshy.

*Time to develop roots.*—2 months.

*Crop time* (1 *liter container*).—From 18 to 24 months from a division.

Foliage:

*Branching pattern.*—Dense basal branching rosette formed by many fan-shaped divisions. A single fan divides into 6-8 fans during the growing season. A one year old plant comprises 6-8 fans.

*Foliage type.*—Evergreen.

*Quantity of leaves.*—30-40, typically 5 leaves per fan.

*Leaf width* (*widest point*).—13 mm.

*Leaf length.*—Ranges from 25 cm. to 35 cm. in length.

*Leaf thickness.*—2 mm at the midrib.

*Leaf arrangement.*—Equitant.

*Leaf shape.*—Gladiate.

*Leaf division.*—Simple.

*Leaf attachment.*—Basally sheathing.

*Leaf apex.*—Acute.

*Leaf base.*—Truncate.

*Leaf margin.*—Entire.

*Leaf form.*—Reflexing. Approximately one third of the entire leaf length extends below the base of the plant.

*Leaf coloration.*—Leaves are variegated consisting of parallel bands of differing color. The following widths of each colored band are measured at the widest point of the leaf.

*Leaf blade color* (*adaxial surface*).—Outermost bands (width 0.5 mm, extending inward from each margin to a distance of 0.5 mm from the margin): 187A. Second bands (width 2.0 mm, commencing at distance of 0.5 mm from each margin and extends to distance of 2.5 mm from each margin): 131A, 131B and 131C are all present. Central band (width 8 mm, commencing at distance of 2.5 mm from one margin and extends through the middle of the leaf to distance of 2.5 mm from the other margin): 2D.

*Leaf blade color* (*abaxial surface*).—As adaxial surface except central band, 145B.

*Leaf blade surface* (*adaxial surface*).—Matte, minutely furrowed.

*Leaf blade surface* (*abaxial surface*).—Matte, minutely furrowed.

*Leaf pubescence* (*adaxial and abaxial surfaces*).—None observed.

*Venation pattern.*—Except for mid-vein on abaxial surface, veins are barely visible. Veins parallel, very narrow, hair-like, approximately 0.3 mm apart, color appears closest to 138B. Mid-vein, abaxial surface: Approximately 0.25 mm in width, color 64B.

*Leaf fragrance.*—No fragrance observed.

*Other significant leaf traits.*—Flattened cross section from apex to middle of leaf length, becoming increasingly folded towards base. Folds become fused at base.

Flower: No flowers have been observed by the inventor on the oldest (five years) plants.

The invention claimed is:

1. A new and distinct cultivar of *Phormium* plant named 'BLONDIE' as described and illustrated herein.

* * * * *